United States Patent [19]
Tsuji et al.

[11] Patent Number: 6,039,555
[45] Date of Patent: Mar. 21, 2000

[54] LIQUID-PERMEABLE TOPSHEET FOR BODY EXUDATES ABSORBENT ARTICLE, APPARATUS AND METHOD FOR MANUFACTURING SAME

[75] Inventors: Tomoko Tsuji, Kagawa-ken; Hisashi Takai, Ehime-ken; Hiroki Goda, Kagawa-ken, all of Japan

[73] Assignee: Uni-Charm Corporation, Ehime-ken, Japan

[21] Appl. No.: 09/178,817

[22] Filed: Oct. 26, 1998

Related U.S. Application Data

[62] Division of application No. 08/808,404, Feb. 28, 1997.

[30] Foreign Application Priority Data

Feb. 29, 1996 [JP] Japan ........................................ 8-43223
Feb. 29, 1996 [JP] Japan ........................................ 8-43224

[51] Int. Cl.⁷ .......................... B29C 43/32; B29C 43/44; B29C 43/46
[52] U.S. Cl. .......................... 425/362; 425/363; 492/30; 492/33; 264/284
[58] Field of Search ........................ 156/209; 492/30, 492/33, 36; 264/284, 263, 293; 425/363, 369, 362

[56] References Cited

U.S. PATENT DOCUMENTS

| | | |
|---|---|---|
| 2,662,246 | 12/1953 | Klugh et al. ............................. 425/335 |
| 3,095,878 | 7/1963 | Bassett . |
| 3,922,329 | 11/1975 | Kim et al. ................................ 264/147 |
| 4,614,679 | 9/1986 | Farrington, Jr. et al. . |
| 4,741,941 | 5/1988 | Englebert et al. . |
| 5,439,459 | 8/1995 | Tanji et al. . |
| 5,613,962 | 3/1997 | Kenmochi et al. . |
| 5,628,844 | 5/1997 | Nishino et al. . |
| 5,656,232 | 8/1997 | Takai et al. . |

FOREIGN PATENT DOCUMENTS

| | | |
|---|---|---|
| 57-82505 | 5/1982 | Japan . |
| 7-328061 | 12/1995 | Japan . |
| 2186233 | 8/1987 | United Kingdom . |

*Primary Examiner*—Richard Crispino
*Assistant Examiner*—Sue A. Purvis
*Attorney, Agent, or Firm*—Lowe Hauptman Gopstein Gilman & Berner

[57] ABSTRACT

A topsheet for body exudates absorbent article includes a hydrophilic nonwoven fibrous sheet and a plurality of thermoplastic synthetic resin filaments extending in one direction parallel to one another and continuously bonded to an upper surface of the nonwoven fibrous sheet so that a composite sheet of these sheet and filaments have crests and troughs alternately repeating longitudinally of the filaments and respectively extend transversely of the filaments. An apparatus and a method for manufcturing the topsheet are also disclosed, wherein a pair of mutually engageable embossing rolls are used for forming the crests and the troughs onto the coposite sheet.

3 Claims, 6 Drawing Sheets

LIQUID-PERMEABLE TOPSHEET FOR BODY EXUDATES ABSORBENT ARTICLE, APPARATUS AND METHOD FOR MANUFACTURING SAME

This application is a Divisional of application Ser. No. 08/808,404 filed Feb. 28, 1997.

BACKGROUND OF THE INVENTION

The present invention relates to a liquid-permeable topsheet for a body exudates absorbent article such as a sanitary napkin or a disposable diaper, an apparatus and a method for manufacturing the topsheet.

Japanese Laid-Open Patent Application No. Sho57-82505 discloses a disposable diaper having a topsheet composed of a hydrophobic net-like sheet of thermoplastic synthetic resin and a hydrophilic sheet such as a nonwoven fibrous sheet. The hydrophobic net-like sheet is placed on the hydrophilic sheet and these sheets are integrally bonded together by subjecting them to a heat-embossing treatment.

Japanese Laid-Open Patent Application No. Hei7-328061 discloses a body exudates absorbent article such as a sanitary napkin having a topsheet composed of a liquid-permeable nonwoven fibrous sheet and a plurality of parallel lines of film strips of thermoplastic synthetic resin. The film strips are place don an upper surface of the liquid-permeable nonwoven fibrous sheet and these are integrally heat-sealed under pressure so that regions of the nonwoven fibrous sheet exposed between each pair of adjacent film strips may retain liquid-permeability.

In these known topsheets, the net-like sheet and the film strips certainly serve to improve a strength of the topsheet, to control a direction in which body exudates flow within the topsheet and to conceal menstrual discharge absorbed in an absorbent core of an article such as a diaper or a sanitary napkin.

However, in these known topsheets obtained by welding the net-like sheet or the film strips onto the nonwoven fibrous sheet, welded areas tend to have a higher rigidity than that at non-welded areas and thereby tend to deteriorate softness of the topsheet as a whole. In consequence, these topsheets are necessarily poor fitting, uncomfortable to wear and cause leakage of body exudates from the article.

SUMMARY OF THE INVENTION

In view of the foregoing problems, it is a principal object of the invention to allow a plurality of filaments of thermoplastic synthetic resin to be continuously bonded to an upper surface of a nonwoven fibrous sheet of thermoplastic synthetic resin in order to obtain a liquid-permeable topsheet without deteriorating softness of the topsheet due to such bonding or, if any, with such deterioration acceptably alleviated.

A liquid-permeable topsheet for a body exudates absorbent article, according to the invention, comprises:

a liquid-permeable nonwoven fibrous sheet of thermoplastic synthetic resin and a plurality of filaments of thermoplastic synthetic resin;

the filaments extending in one direction parallel to one another and continuously bonded to an upper surface of the nonwoven fibrous sheet longitudinally thereof, and a composite sheet of these nonwoven fibrous sheet and filaments describing undulations having crests and troughs both extending transversely of the filaments and alternately repeating longitudinally of the filaments at a predetermined pitch.

An apparatus for manufacturing a liquid-permeable topsheet for body exudates absorbent article according to the invention comprises:

a pair of mutually engageable embossing means for an embossing treatment of a continuous composite sheet web composed of a liquid-permeable nonwoven fibrous sheet of thermoplastic synthetic resin and a plurality of filaments of thermoplastic synthetic resin extending in one direction parallel to one another and continuously bonded to an upper surface of the nonwoven fibrous sheet longitudinally thereof;

the embossing means including a first roll and a second roll;

the first roll being provided on a circumferential surface thereof with cones arranged in a plurality of lines extending in an axial direction thereof as well as in a circumferential direction thereof;

the second roll being provided on a circumferential surface thereof with crests of an inverted V-shaped cross-section and troughs of a V-shaped cross-section arranged in a plurality of lines in an axial direction thereof so that the crests and troughs are alternatively arranged in a circumferential direction thereof; and wherein a line of the cones of the first roll arranged in the axial direction thereof is received by the corresponding trough of the second roll while the crest of the second roll is received between two lines of cones which are adjacent to each other in the circumferential direction thereof.

A method for manufacturing a liquid-permeable topsheet for body exudates absorbent article according to the invention comprises the steps of:

composing a continuous composite sheet web by integrally bonding a plurality of filaments of thermoplastic synthetic resin onto a surface of a nonwoven fibrous sheet of thermoplastic synthetic resin so that the filaments is spaced apart from and in parallel to one another along a longitudinal direction thereof; and feeding the composite sheet web into a space between a pair of mutually engageable embossing means for an embossing treatment, while the filaments remain in a thermally softened state.

In the topsheet according to the invention, both the upper surface of the nonwoven fibrous sheet and the filaments continuously bonded thereto present the crests and the troughs alternately appearing longitudinally of the filaments and respectively extending transversely of the filaments. Such topsheet can be easily curved longitudinally of the filaments and relatively soft, since the crests and the troughs form a bellows-like structure. Body exudates absorbent article using this topsheet is easily curved in conformity with a contour of the wearer's body to achieve a good fitness to the wearer's skin.

According to the embodiment in which the fiber density of the nonwoven fibrous sheet progressively increases from the crest to the trough, body exudates can easily spread from the crest toward the trough. In view of a fact that the trough tends to be spaced from the wearer's skin, body exudates discharged on the topsheet rapidly go away from the wearer's skin into the core. Accordingly, an undesirable feeling of wetness during use of the body exudates absorbent article is effectively alleviated by use of such topsheet for such article.

According to the embodiment in which the topsheet includes an opening of relatively large dimension in the bottom of each trough, fibers around such opening extend downward in contact with the core and promote body exudates collected in each trough to move into the core. With a consequence, an undesirable feeling of wetness experienced by the wearer of the body exudates absorbent article is further alleviated by use of such topsheet for the article. Particularly when a fiber density is adjusted to be relatively high around the opening, the feeling of wetness is more significantly alleviated.

When the lower side of the topsheet has convexities, the bottom of each trough is well kept in close contact with the liquid-absorbent core and promotes body exudates collected in this trough to move into the core.

Other and further objects, features and advantages of the invention will appear more fully more the following discription.

DESCRIPTION OF PREFERRED EMBODIMENTS

Figure 1:
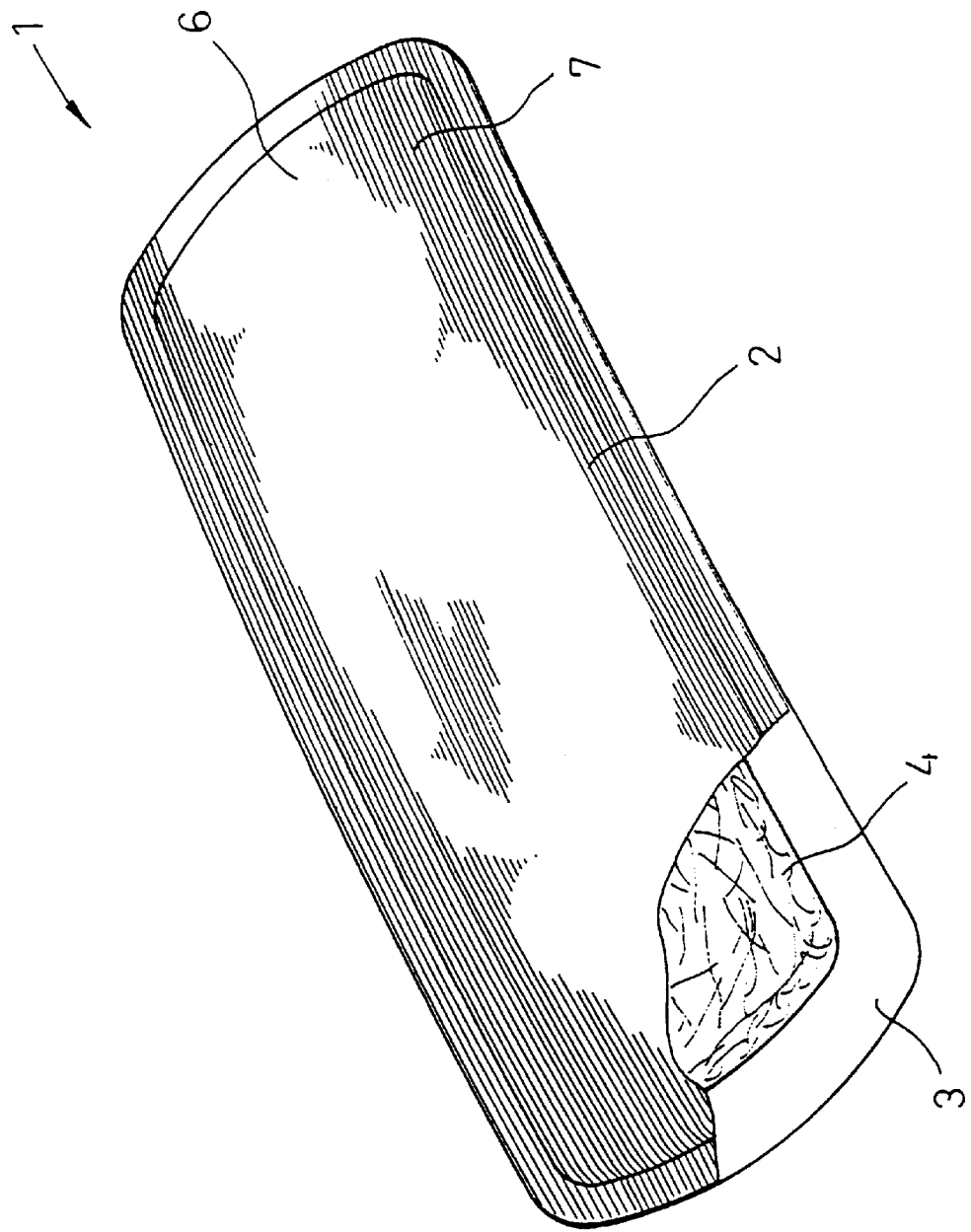
FIG. 1 is a perspective view of a sanitary napkin as partially broken away.

Sanitary napkin 1 shown by FIG. 1 in a perspective view as partially broken away comprises a liquid-permeable topsheet 2, a liquid-impermeable backsheet 3 and a liquid-absorbent core 4 disposed therebetween. The topsheet 2 and backsheet 3 are bonded to each other in their regions extending outward beyond a peripheral edge of the core 4. The topsheet 2 comprises a nonwoven fibrous sheet 6 and a plurality of filaments 7 bonded to and extending on an upper surface of the nonwoven fibrous sheet 6 parallel to one another longitudinally of the napkin 1.

Figure 2:
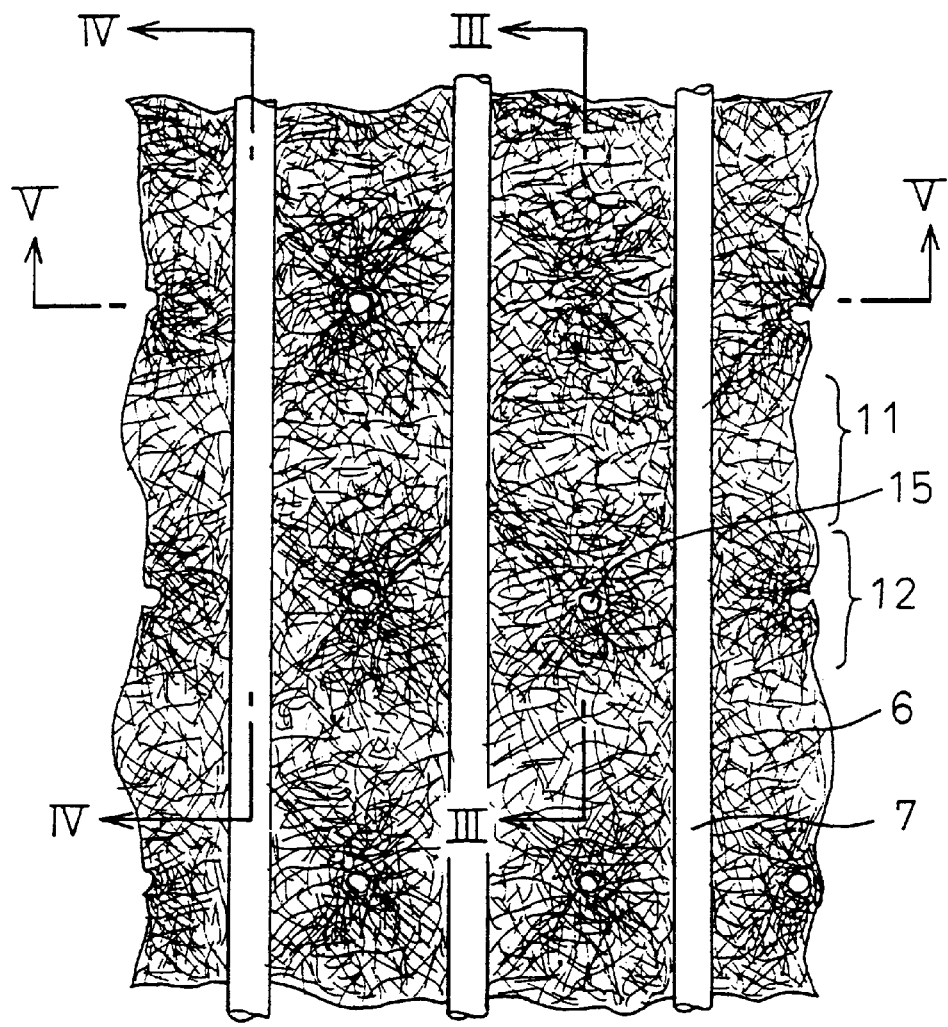
FIG. 2 is a fragmentary scale-enlarged plan view of a topsheet.
Figure 3:
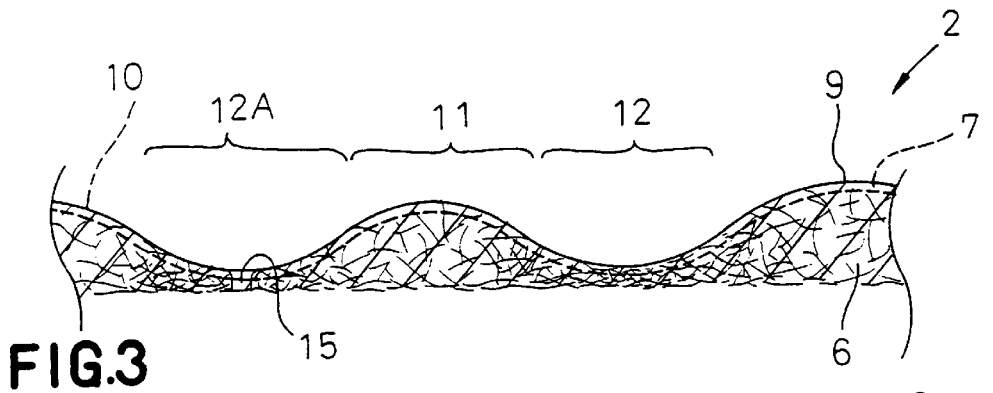
FIG. 3 is a sectional view taken along line III—III in FIG. 2.
Figure 4:
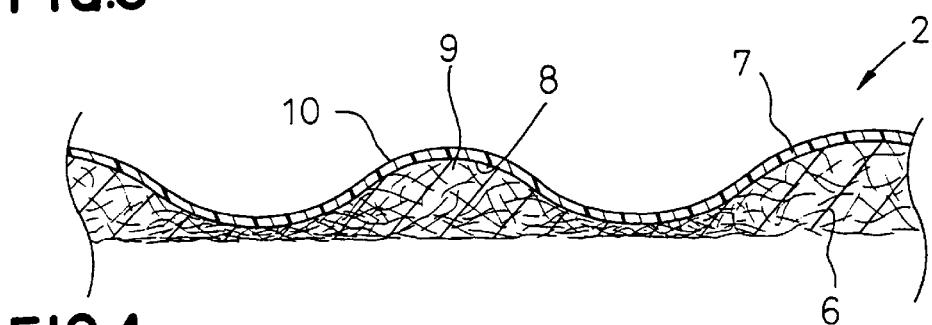
FIG. 4 is a sectional view taken along line IV—IV in FIG. 2.

FIGS. 2, 3 and 4 are respectively a fragmentary scale-enlarged plan view, a sectional view taken along line III—III and a sectional view taken along line IV—IV both in FIG. 2. The nonwoven fibrous sheet 6 is formed by treating thermoplastic synthetic fibers so as to become hydrophilic and to be entangled or intertwined. The filaments are formed of thermoplastic synthetic resin and have lower surfaces 8 continuously bonded to an upper surface 9 of the nonwoven fibrous sheet 6. Each filament 7 is spaced apart from the adjacent filament by a predetermined distance.

Figure 5:
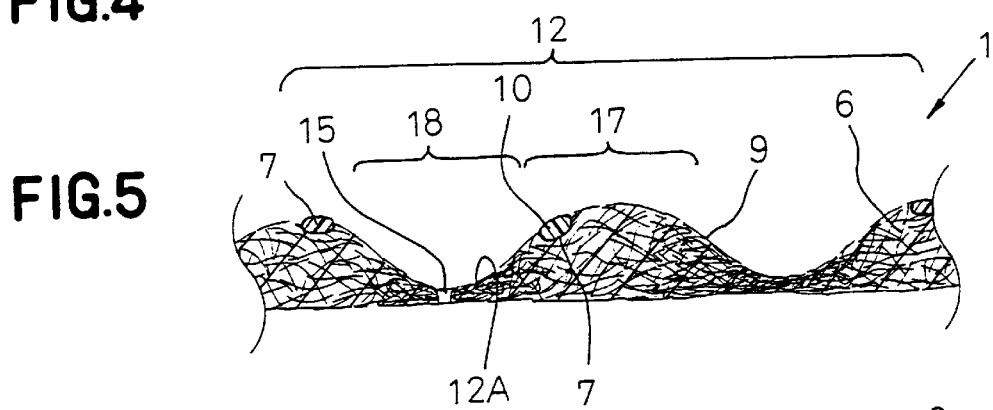
FIG. 5 is a sectional view taken along line V—V in FIG. 2.

As will be apparent from FIGS. 3 and 4, the upper surface 9 of the nonwoven fibrous sheet 6 and the filaments 7 have crests 11 and troughs 12 alternately appearing at a predetermined period in a longitudinal direction of the filaments 7. These crests 11 and troughs 12 extend transversely of the filaments 7, i.e., transversely of the napkin 1 as viewed in FIG. 1. As it is best seen in FIG. 5, between each pair of adjacent filaments 7, the upper surface 9 of the nonwoven fibrous sheet 6 may be substantially the same level as apices 10 of the filaments 7 or at the level higher than the apices 10. A fiber density of the nonwoven fibrous sheet 6 may progressively increase from the crest 11 to the adjacent trough 12, as shown by FIGS. 3 and 4 (cf. the darkest portions), or may remain substantially uniform. Alternatively, the fibers may be locally sparse at a bottom of each trough 12 so as to form an opening 15 passing through the nonwoven fibrous sheet 6 as seen in FIGS. 2 and 3. Sometimes the fiber density may be relatively high around the opening 15. Such opening 15 is shown in associated with the trough 12A in FIG. 3.

It will be apparent from FIG. 5, which is a sectional view taken along line V—V in FIG. 2, that the trough 12 has the second crest 17 and the second trough 18 alternately repeating in its longitudinal direction (from the left hand to the right hand as viewed in FIG. 2). It should be understood that a height of the second crest 17 does not exceed a height of the crest 11. The second trough 18 may have its fiber density higher than that of the crest 17 and may have the opening 15 as shown by FIGS. 2 and 3.

Figure 6:
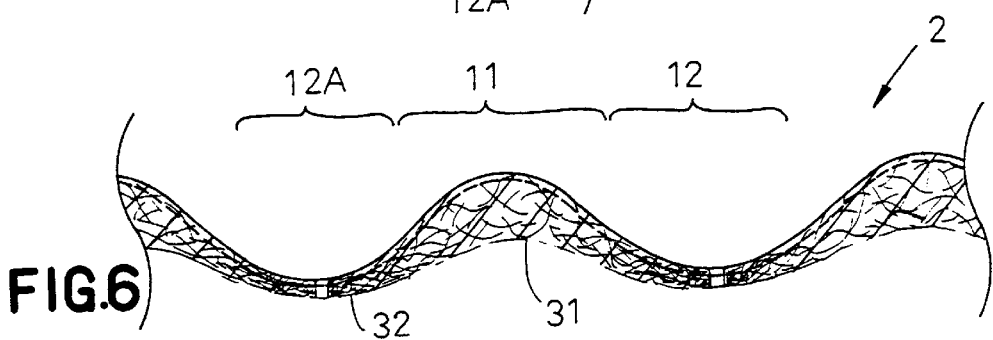
FIG. 6 is a view similar to FIG. 3 but showing a variant of the topsheet.
Figure 7:
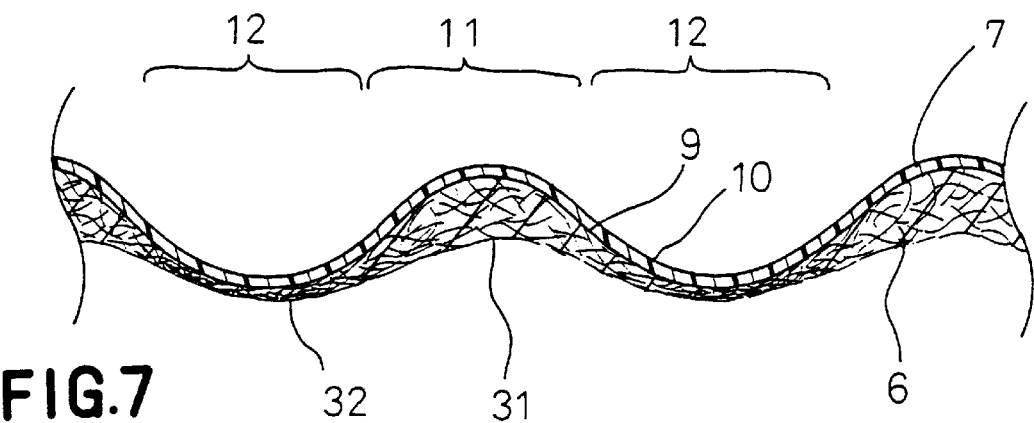
FIG. 7 is a view similar to FIG. 4 but showing a variant of the topsheet.

FIGS. 6 and 7 show a variant of the topsheet 2 in a sectional view similar to FIGS. 3 and 4, respectively. According to this variant of the topsheet 2, its upper surface is similar to that in the topsheet 2 shown by FIG. 3 but its lower surface is not flat. More specifically, a lower surface of the crest 11 is formed with a concavity 31 while a lower surface of the trough 12 is formed with a convexity 32.

The sanitary napkin 1 employing the topsheet 2 of such arrangement can be smoothly curved in conformity with a contour of the wearer's body with a good fitness because the topsheet 2 behaves as bellows formed by the crests 11 and the troughs 12. Most of menstrual discharge moves from the low fiber density regions to the high fiber density regions, specifically to say, spreads from the crests 11 to the troughs 12, then from the bottoms of the troughs 12 into the core 4. During use of the napkin 1, the topsheet 2 tends to be maintained in contact with the wearer's skin principally at the crests 11 and to be spaced from the wearer's skin at the troughs 12. As a result, menstrual discharge spreading into the troughs 12 gets away from the wearer's skin and this phenomenon advantageously contributes to alleviate an uncomfortable feeling of wetness which otherwise would be experienced by the wearer. Forming the bottom of each trough 12 with the opening 15 of a sufficiently large dimension allows menstrual discharge staying in this trough 12 to be more rapidly moved to the core 4. Particularly in the embodiment of the topsheet 2 shown by FIG. 6, a peripheral region of each opening 15 is sufficiently kept in contact with the core 4 to promote a desired movement of menstrual discharge. When the upper surface 9 of the nonwoven fibrous sheet 6 lies at substantially the same level as the apices 10 of the filaments 7 or at a level higher than the apices 10, a touch peculiar to synthetic resin can be effectively alleviated and the topsheet 2 as a whole can provide a cloth-like touch, since direct contact of the filaments 7 with the wearer's skin can be reduced. The topsheet 2 having undulations on either side thereof as seen in FIG. 6 serves to improve a cushioning effect when the topsheet 2 comes in contact with the wearer's skin.

Figure 8:
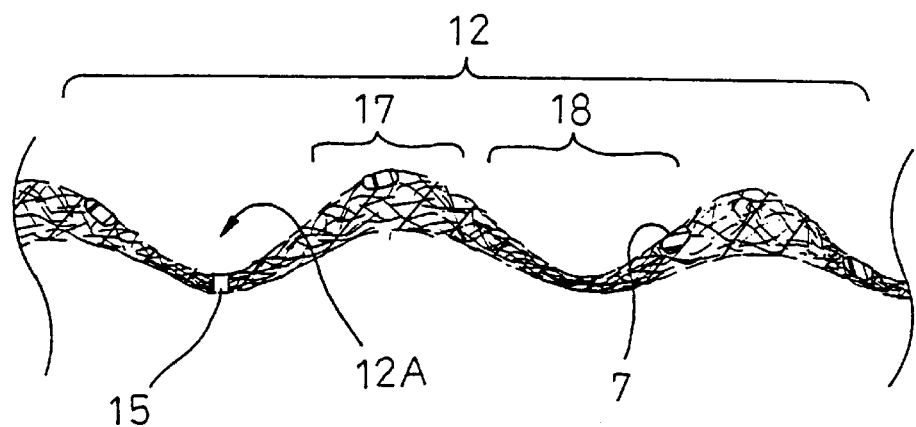
FIG. 8 is a view similar to FIG. 5 but showing a variant of the topsheet.

FIG. 8 shows a variant of the topsheet 2 in a sectional view similar to FIG. 5. In this variant, therefore, the trough 12 has the second crest 17 and the second trough 18 alternately repeating in its longitudinally direction.

An apparatus and a method of manufacturing the topsheet 2 shown in FIGS. 6, 7 and 8 will be briefly described. First of all, a continuous sheet web of nonwoven fibrous sheet adapted to become the individual nonwoven fibrous sheets 6 is fed in one direction at a predetermined velocity. On the other hand, an extruder (not shown) is used to extrude a plurality of continuous filaments adapted to form a part of the individual topsheets 2 so that these filaments are placed on an upper surface of the web parallel to one another along a direction in which the web is fed and in the same velocity as that of the web. The web and the filaments are subjected to an embossing treatment while the filaments are in a softened state thereof so that they are integrally bonded together and, at the same time, crests and troughs designed to form the crests 11 and the troughs 12 in the individual topsheets 2 are shaped. In this way, a continuous composite sheet web is obtained. This composite sheet web is cut into the individual topsheets 2.

An example of the continuous sheet web which can be used in this process is a thermal bond nonwoven fibrous sheet made of polyethylene and polypropylene core/sheath conjugated staple fiber (EAC-704V06, ES fiber manufactured by CHISSO CORPORATION in Japan) of which a fineness is 1~10 d, and a length is 30~100 mm, and has a basic weight of 10~40 g/m$^2$, an apparent thickness of 0.1~0.4 mm and a fiber surface treated to have a desired hydrophilicity. An example of the continuous filaments which can be used in this process have a width of 0.1~1.0 mm and a thickness of 0.01~0.07 mm extruded from a mixture of 95~60% by weight of low density polyethylene (EXCELLEN VL800 manufactured by SUMITOMO CHEMICAL COMPANY, LIMITED in Japan) having a density of 0.905~0.93 and a melt flow rate of 10~25 and 5~40% by weight of an auxiliary agent serving to facilitate the formation of filaments, microcrystalline wax serving as a blood repellent agent and TiO$_2$ as a colorant, etc. These filaments are preferably place don the web parallel to and being spaced apart from one another by 0.3~2 mm.

Figure 9:
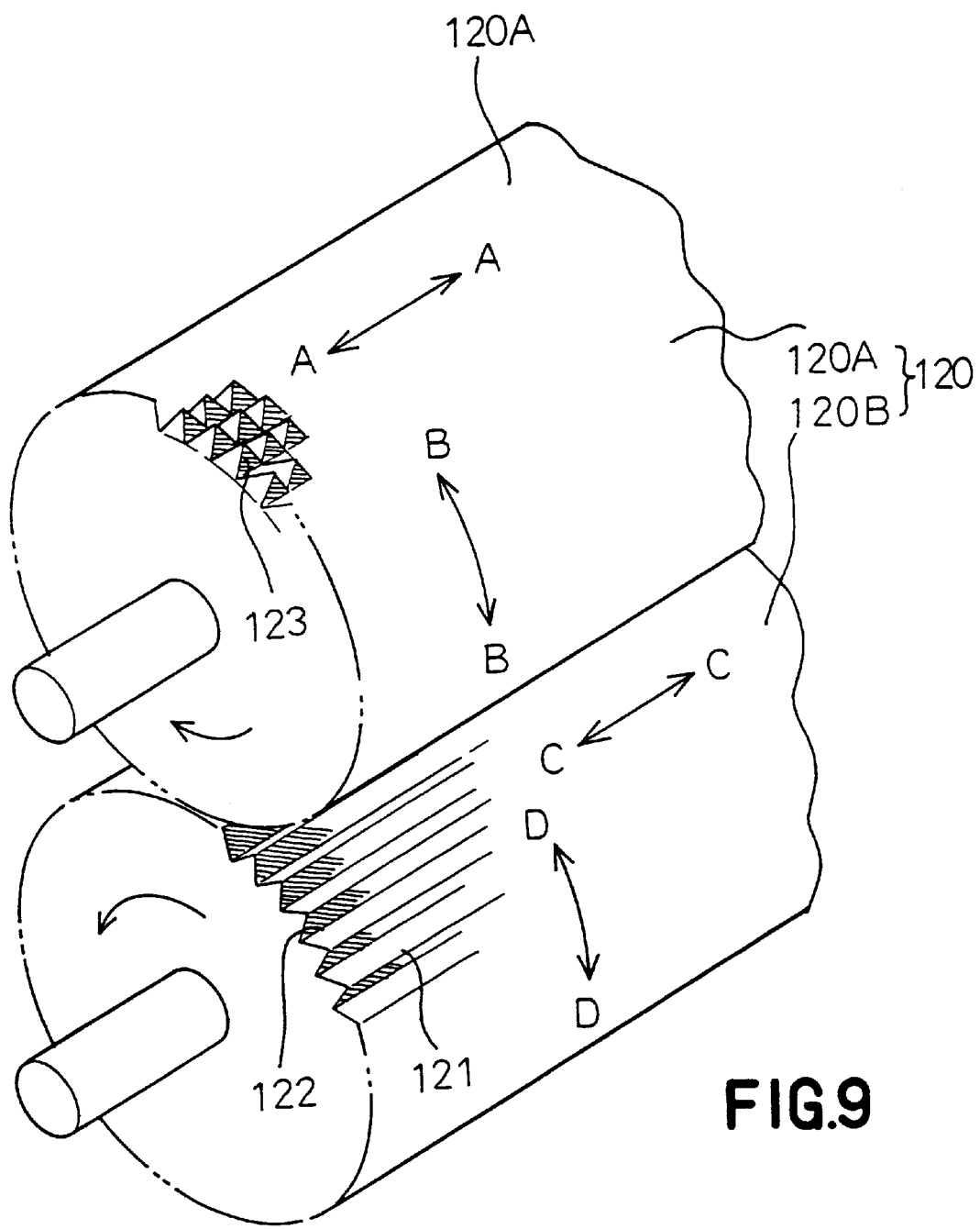
FIG. 9 is a schematic perspective view of a pair of embossing rolls.
Figure 10:
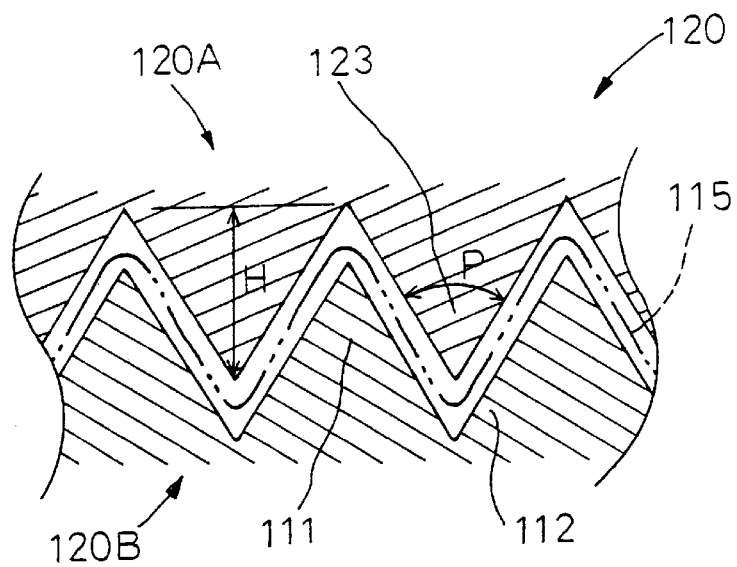
FIG. 10 is a side view of the pair of embossing rolls as they are engaged with each other.

FIG. 9 is a schematic perspective view showing, as partially broken away, embossing roll means 120 used to form the crests and the troughs in the composite sheet web and FIG. 10 is a fragmentary side view thereof, in which the composite sheet web is indicated by an imaginary line and designated by reference numeral 115. The embossing roll means 120 comprise an upper roll 120A and a lower roll 120B. The upper roll 120A is provided with pyramidal cones 123 arranged in a plurality of lines extending in an axial direction A—A as well as in a circumferential direction B—B of the roll 120A. The lower roll 120B, on the other hand, is provided with crests 121 of an inverted V-shaped cross-section and troughs 122 of a V-shaped cross-section arranged in a plurality of lines in an axial direction C—C so that the crests 121 and troughs 122 are alternately arranged in a circumferential direction D—D of the roll 120B. The upper and lower rolls 120A, 120B are engaged with each other as they rotate clockwise and counterclockwise, respectively. Specifically to say, a line of pyramidal cones 123 of the upper roll 120A arranged in the axial direction A—A thereof are received by the corresponding trough 122 of the lower roll 120B as the line of pyramidal cones 123 have rotated down to a bottom position as viewed in FIG. 9 whereupon the crest 121 of the lower roll 120B is received between two lines of pyramidal cones which are adjacent to each other in the circumferential direction B—B.

Figure 11:
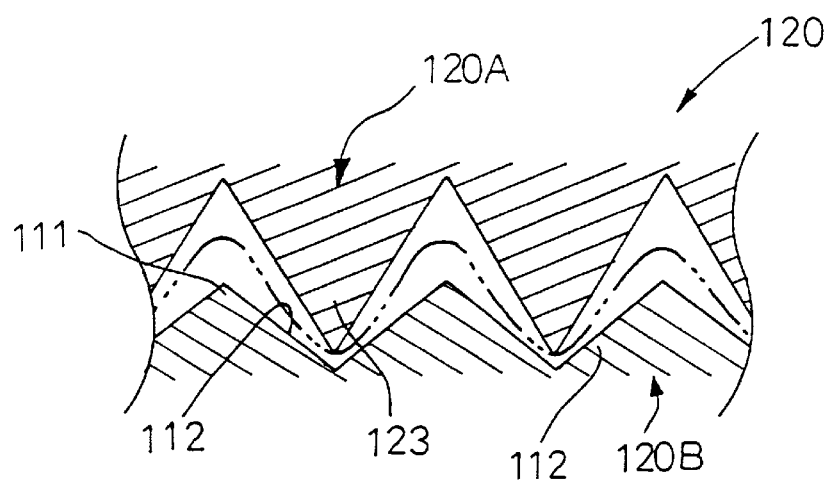
FIG. 11 is a side view of an alternative pair of embossing rolls as they are engaged with each other.
Figure 12:
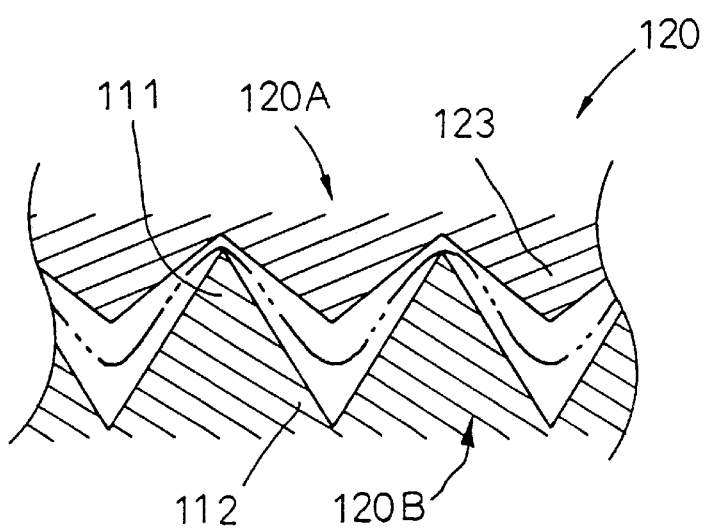
FIG. 12 is a side view showing still another pair of embossing rolls as they are engaged with each other.

FIGS. 10, 11 and 12 illustrate various manners in which the upper and lower rolls 120A, 120B are engaged with each other. In the case illustrated by FIG. 10, each pyramidal cone 123 of the upper roll 120A has substantially the same cross-section as those of the crest 111 and the trough 112 of the lower roll 120B, so that a gap formed between the upper and lower rolls 120A, 120B is substantially uniform. In the case illustrated by FIG. 11, the gap formed between the upper and lower rolls 120A, 120B varies from the minimum between an apex of each pyramidal cone 123 and a bottom of the corresponding trough 112 to the maximum between a base of each pyramidal cone 123 and an apex of the corresponding crest 111. In the case illustrated by FIG. 12, the gap varies from the minimum between the base of each pyramidal cone 123 and the apex of the corresponding crest 111 to the maximum between the apex of each pyramidal cone 123 and the bottom of the corresponding trough 112. In these embodiments, the pyramidal cone 123 of the upper roll 120A is preferably configured so that its circumferential cross-section passing the apex of the cone 123 preferably has its included angle P (cf. FIG. 10 of 30~70° and a height H of 1~5 mm). The crests 111 and the troughs 112 of the lower roll 120B may be dimensioned so as to achieve any one of the manners illustrated by FIGS. 10, 11 and 12. An included angle of the pyramidal cone 123 in its axial cross-section may be same as or different from the included angle P.

By embossing the composite sheet web 115 by the upper and lower rolls 120A, 120B, spots on an upper surface of the composite sheet 115 pressed by the pyramidal cones 123 are significantly depressed in a funnel-shape and undersides of these spots project downward. Lower ends of these projections are sometimes crashed through under a pressure exerted by the apices of the pyramidal cones 123 and, in consequence, individual fibers of the sheet web 115 are fluffed downward or forcibly spaced from one another to form the openings 15. The apices of the pyramidal cones 123 are intermittently arranged axially of the upper roll 120A, so the funnel-shaped depressions of the sheet 115 and the corresponding projections on an underside thereof are intermittently arranged transversely of the sheet. In this way, the sectional configurations shown by FIGS. 5 through 8 are obtained. The trough group 12 of the topsheet 2 is formed by a line of the pyramidal cones 123 and the second trough 18 of the trough group 12 and the convexity underlying the troughs 18 are formed by the individual pyramidal cones 123. The openings 15 in the trough group 12 are formed by the apices of the pyramidal cones 123.

The composite sheet web 115 subjected to the embossing treatment as described above is now cut in a predetermined dimension to be used as the topsheet 2 of the sanitary napkin 1. It should be understood that the pressing force exerted by the pyramidal cones 123 sometimes causes the individual fibers to hang down from the convexities 32 on the lower surface of the sheet web 115 and these fibers may be intertwined with individual fibers of the liquid-absorbent core 4 to prevent the topsheet 2 from being readily spaced from the core 4. Furthermore, the filaments of the composite sheet web 115 advantageously prevent the structure of the nonwoven fibrous sheet from being disturbed before and after the embossing treatment.

Though an apparatus and a method for manufacturing the topsheet 12 shown in FIGS. 3, 4 and 5 is not illustrated here, this topsheet 15 can be obtained by treating it with the upper roll 120A and a lower roll having a smooth surface of appropriate hardness made of paper, nonwoven fibrous sheet, plastic or rubber, etc. in place of the lower roll 120B.

It should be understood that the process according to the invention is not limited to use of the above-mentioned pyramidal cones 123 but the cones of any other types such as trigonal pyramids may be used without departing from the spirit and the scope of the invention.

The entire disclosures of Japanese Patent Application Nos. Hei8-43223 and Hei8-43224 filed on Feb. 29, 1996 including specification, drawings and abstract are herein incorporated by reference in their entireties.

What is claimed is:

1. An apparatus for manufacturing a liquid-permeable topsheet for body exudates absorbent article comprises:

a pair of mutually engageable embossing elements for an embossing treatment of a continuous composite sheet web composed of a liquid-permeable nonwoven fibrous sheet of thermoplastic synthetic resin and a plurality of filaments of thermoplastic synthetic resin extending in one direction parallel to one another and continuously bonded to an upper surface of the nonwoven fibrous sheet;

the embossing elements including a first roll and a second roll;

the first roll being provided on a circumferential surface thereof with cones arranged in a plurality of lines, extending in an axial direction thereof as well as in a circumferential direction thereof;

the second roll being provided on a circumferential surface thereof with crests of an inverted V-shaped cross-section and troughs of a V-shaped cross-section arranged in a plurality of lines in an axial direction thereof so that the crests and troughs are alternatively arranged in a circumferential direction thereof; and wherein a line of the cones of the first roll arranged in the axial direction thereof is received by the corresponding trough of the second roll while the crest of the second roll is received between two lines of cones which are adjacent to each other in the circumferential direction thereof.

2. An apparatus according to claim 1, wherein the cones are pyramidal cones or circular cones.

3. An apparatus according to claim 1, wherein the apparatus further comprises an extruder for continuously extruding the filaments.

* * * * *